(12) United States Patent
Panneer Selvam

(10) Patent No.: US 11,064,911 B2
(45) Date of Patent: Jul. 20, 2021

(54) STANDING DESK BIOMETRICS

(71) Applicant: VitalTech Properties, LLC, Plano, TX (US)

(72) Inventor: Anjan Panneer Selvam, Plano, TX (US)

(73) Assignee: VitalTech Properties, LLC, Plano, TX (US)

( * ) Notice: Subject to any disclaimer, the term of this patent is extended or adjusted under 35 U.S.C. 154(b) by 0 days.

(21) Appl. No.: 16/712,510

(22) Filed: Dec. 12, 2019

(65) Prior Publication Data

US 2020/0187831 A1 Jun. 18, 2020

Related U.S. Application Data

(60) Provisional application No. 62/778,638, filed on Dec. 12, 2018.

(51) Int. Cl.
*G08B 21/22* (2006.01)
*A61B 5/11* (2006.01)
*A47B 9/00* (2006.01)

(52) U.S. Cl.
CPC .............. *A61B 5/1116* (2013.01); *A47B 9/00* (2013.01); *A47B 2200/0062* (2013.01); *A47B 2220/0091* (2013.01)

(58) Field of Classification Search
CPC .............. A47B 2200/0062; A47B 9/00; A47B 2220/0091; A47B 17/033; A47B 2037/005; A47B 21/02; A47B 2200/0085; A47B 2200/0086; A47B 2009/006; A47B 2200/0039; A47B 2200/0056; A47B 2200/0061; A47B 83/02; G06Q 10/00; G06Q 10/063114; A61B 5/1116; A61B 5/002; A61B 5/0022; A61B 5/02055; A61B 5/7221; A61B 5/7275; A61B 5/4561; A61B 5/6891; G01C 19/34; G01C 19/44; G01C 21/165; G01S 5/15; G06F 1/1686; G06F 1/1694; G06F 3/011; G06F 1/1601; G06F 1/1605; G06F 2200/1612; G06F 3/012; G06F 21/32; G06F 21/34; G06F 21/602; G06F 21/6245; G06F 19/00;
(Continued)

(56) References Cited

U.S. PATENT DOCUMENTS 5,931,102 A * 8/1999 Grahl .................. A47B 17/033
108/143
6,336,900 B1 1/2002 Alleckson et al.
(Continued)

FOREIGN PATENT DOCUMENTS

CN 206214083 U 6/2017
CN 106999048 A 8/2017
(Continued)

OTHER PUBLICATIONS

International Search Report and Written Opinion, PCT/US2019/047929, dated Nov. 18, 2019, pp. 1-15.

*Primary Examiner* — Daniel Previl
(74) *Attorney, Agent, or Firm* — Goodhue, Coleman & Owens, P.C.

(57) ABSTRACT

A standing desk system, method, and device. A user is detected proximate a standing desk. A position and orientation of the user are determined. Time periods associated with the position and the orientation are detected.

20 Claims, 6 Drawing Sheets

(58) Field of Classification Search
CPC ........... G06K 9/00496; G06K 9/00778; G06K 9/00013; G06K 9/00604; G06K 9/00087; G06K 9/00154; G06K 9/00221; G06K 9/00617; G06K 9/00892; G06K 9/00912; G06K 9/00926; G06K 9/036; G06K 9/2018; G06K 9/2027; G06K 9/38; G09G 2320/028; G09G 3/32; G16H 20/30; G16H 40/60; G16H 40/63; G16H 50/30; H04L 67/24; H04L 63/083; H04L 63/107; H04L 9/3231; H04M 1/72522; H04W 4/029; H04W 4/33; H04W 8/005; H04W 12/04031; H04W 12/08; H04W 4/80; H04W 84/12; H04W 4/021; H04W 4/026; H04W 4/18; A47L 11/24; A47L 11/4011; A47L 11/4036; A47L 11/4061; A47L 2201/022; A47L 2201/04; A47L 9/2873; B60L 15/20; B60L 15/2036; B60L 1/003; B60L 2200/40; B60L 2220/44; B60L 2240/14; B60L 2240/32; B60L 2240/421; B60L 2240/423; B60L 2240/461; B60L 2240/463; B60L 2240/465; B60L 2240/62; B60L 2250/16; B60L 2260/32; B60L 3/106; B60L 50/52; B60L 50/66; B60L 53/14; B60L 58/21; F16M 11/04; F16M 11/10; F16M 11/2014; F16M 11/2092; F16M 11/24; F16M 13/00; F16M 13/02; F16M 13/022; F16M 2200/027; F16M 2200/068; G01D 21/02; G05D 1/0219; G05D 1/0234; G05D 2201/0203; Y02T 10/645; Y02T 10/7005; Y02T 10/7061; Y02T 10/7072; Y02T 10/72; Y02T 10/7275; Y02T 10/7291; Y02T 90/14; Y02T 90/16; Y02T 90/162; G07C 2209/02; G07C 9/257; G08B 21/22; H04Q 2209/823; H04Q 9/04; H04N 7/183
USPC ............. 340/573.1, 539.23, 539.26, 539.13, 340/539.11, 571, 572.1, 677, 686.6, 340/691.6, 692, 825.36
See application file for complete search history.

(56) References Cited

U.S. PATENT DOCUMENTS

| | | | |
|---|---|---|---|
| 7,539,532 B2 | 5/2009 | Tran | |
| 7,539,533 B2 | 5/2009 | Tran | |
| 7,558,622 B2 | 7/2009 | Tran | |
| 7,976,386 B2 | 7/2011 | Tran | |
| 8,108,036 B2 | 1/2012 | Tran | |
| 8,121,673 B2 | 2/2012 | Tran | |
| 8,323,189 B2 | 12/2012 | Tran et al. | |
| 8,328,718 B2 | 12/2012 | Tran | |
| 8,425,415 B2 | 4/2013 | Tran | |
| 8,449,471 B2 | 5/2013 | Tran | |
| 8,475,368 B2 | 7/2013 | Tran et al. | |
| 8,500,636 B2 | 8/2013 | Tran | |
| 8,652,038 B2 | 2/2014 | Tran et al. | |
| 8,684,922 B2 | 4/2014 | Tran | |
| 8,727,978 B2 | 5/2014 | Tran et al. | |
| 8,747,313 B2 | 6/2014 | Tran et al. | |
| 8,764,651 B2 | 7/2014 | Tran | |
| 8,968,195 B2 | 3/2015 | Tran | |
| 9,060,683 B2 | 6/2015 | Tran | |
| D737,156 S | 8/2015 | Akana et al. | |
| D737,157 S | 8/2015 | Akana et al. | |
| D737,158 S | 8/2015 | Akana et al. | |
| D737,159 S | 8/2015 | Akana et al. | |
| 9,107,586 B2 | 8/2015 | Tran | |
| D741,726 S | 10/2015 | Akana et al. | |
| D744,356 S | 12/2015 | Akana et al. | |
| D745,421 S | 12/2015 | Akana et al. | |
| 9,215,980 B2 | 12/2015 | Tran et al. | |
| D746,707 S | 1/2016 | Akana et al. | |
| D751,070 S | 3/2016 | Akana et al. | |
| D752,044 S | 3/2016 | Akana et al. | |
| D754,793 S | 4/2016 | Akana et al. | |
| D756,357 S | 5/2016 | Akana et al. | |
| D756,822 S | 5/2016 | Akana et al. | |
| D756,823 S | 5/2016 | Akana et al. | |
| D756,824 S | 5/2016 | Akana et al. | |
| D756,825 S | 5/2016 | Akana et al. | |
| D757,722 S | 5/2016 | Akana et al. | |
| D758,219 S | 6/2016 | Akana et al. | |
| D759,011 S | 6/2016 | Akana et al. | |
| D759,725 S | 6/2016 | Akana et al. | |
| D760,716 S | 7/2016 | Akana et al. | |
| D761,793 S | 7/2016 | Akana et al. | |
| 9,392,966 B2 | 7/2016 | Kate | |
| D766,752 S | 9/2016 | Akana et al. | |
| D766,893 S | 9/2016 | Akana et al. | |
| D771,035 S | 11/2016 | Akana et al. | |
| D771,037 S | 11/2016 | Akana et al. | |
| D777,163 S | 1/2017 | Akana et al. | |
| D779,992 S | 2/2017 | Akana et al. | |
| D781,853 S | 3/2017 | Akana et al. | |
| D784,326 S | 4/2017 | Akana et al. | |
| D784,327 S | 4/2017 | Akana et al. | |
| D784,831 S | 4/2017 | Akana et al. | |
| D790,517 S | 6/2017 | Akana et al. | |
| D791,237 S | 7/2017 | Akana et al. | |
| D791,238 S | 7/2017 | Akana et al. | |
| D791,239 S | 7/2017 | Akana et al. | |
| 9,801,542 B2 | 10/2017 | Tran et al. | |
| 9,801,568 B2 | 10/2017 | Ziaie et al. | |
| 9,814,425 B2 | 11/2017 | Tran | |
| 9,820,657 B2 | 11/2017 | Tran | |
| D805,513 S | 12/2017 | Akana et al. | |
| D805,929 S | 12/2017 | Akana et al. | |
| D806,071 S | 12/2017 | Akana et al. | |
| D807,765 S | 1/2018 | Akana et al. | |
| 9,865,176 B2 | 1/2018 | Tran | |
| D809,513 S | 2/2018 | Akana et al. | |
| D812,052 S | 3/2018 | Akana et al. | |
| D816,524 S | 5/2018 | Akana et al. | |
| D817,203 S | 5/2018 | Akana et al. | |
| 9,974,492 B1 | 5/2018 | Dicks et al. | |
| D822,525 S | 7/2018 | Akana et al. | |
| D824,273 S | 7/2018 | Akana et al. | |
| 10,025,908 B1* | 7/2018 | Orellano | G16H 40/63 |
| 10,026,292 B2 | 7/2018 | Baker et al. | |
| 10,051,410 B2 | 8/2018 | Booth et al. | |
| D828,352 S | 9/2018 | Akana et al. | |
| D828,835 S | 9/2018 | Akana et al. | |
| D832,252 S | 10/2018 | Akana et al. | |
| D836,102 S | 12/2018 | Akana et al. | |
| 2013/0058274 A1* | 3/2013 | Scherzer | H04W 12/08 370/328 |
| 2014/0143064 A1 | 5/2014 | Tran | |
| 2014/0249429 A1 | 9/2014 | Tran | |
| 2015/0148623 A1 | 5/2015 | Benaron | |
| 2015/0359467 A1 | 12/2015 | Tran | |
| 2016/0287166 A1 | 10/2016 | Tran | |
| 2016/0338639 A1 | 11/2016 | Myers et al. | |
| 2016/0353880 A1* | 12/2016 | Sigal | G06Q 10/00 |
| 2016/0367202 A1 | 12/2016 | Carter et al. | |
| 2016/0374588 A1* | 12/2016 | Shariff | A61B 5/4875 600/547 |
| 2017/0000387 A1 | 1/2017 | Forth et al. | |
| 2017/0124276 A1 | 5/2017 | Tee | |
| 2017/0213145 A1 | 7/2017 | Pathak et al. | |
| 2017/0354370 A1* | 12/2017 | Hedin | A61B 5/1118 |
| 2018/0064370 A1 | 3/2018 | Ziaie et al. | |
| 2018/0174686 A1 | 6/2018 | Zaphrir et al. | |
| 2018/0177436 A1 | 6/2018 | Chang et al. | |
| 2018/0213928 A1* | 8/2018 | Kassanoff | A47B 41/00 |
| 2018/0333083 A1 | 11/2018 | Orellano | |
| 2019/0004543 A1* | 1/2019 | Kennedy | H04N 5/2351 |

(56) References Cited

U.S. PATENT DOCUMENTS

FOREIGN PATENT DOCUMENTS

| EP | 3346402 A1 | 7/2018 |
|----|------------|--------|
| WO | 2013103570 A1 | 7/2013 |
| WO | 2017190049 A1 | 11/2017 |

* cited by examiner

STANDING DESK BIOMETRICS

PRIORITY STATEMENT

This application claims priority to U.S. Provisional Patent Application No. 62/778,638, filed on Dec. 12, 2018, titled Standing Desk Biometrics hereby incorporated by reference in its entirety.

BACKGROUND

I. Field of the Disclosure

The illustrative embodiments relate to biometrics for standing desk utilization. More specifically, but not exclusively, the illustrative embodiments relate to a system, method, and biosensing wearables for calculating utilization of a standing desk.

II. Description of the Art

Medical information regarding the dangers of prolonged sitting has become clearer in recent years. The health risks associated with excessive sifting are significant. Each year thousands of people suffer workplace injuries or negative effects from excessive sitting. Standing desks have become popular as a way of countering these risks but optimizing efficient usage of standing desks remains difficult.

SUMMARY OF THE DISCLOSURE

The illustrative embodiments provide a standing desk system, method, and standing desk. In one embodiment, a user is detected proximate a standing desk. A position and orientation of the user are determined. Time periods associated with the position and the orientation are detected. In another embodiment, a sensor includes a processor for executing a set of instructions and a memory for storing the set of instructions. The set of instructions are executed to perform the method described.

A sensor for determining standing usage of a platform. The sensor includes a plurality of sensors performing measurements configured to detect a user proximate the plurality of sensors of the platform. The sensor includes a logic engine in communication with the number of sensors that analyze the measurements and communicate usage information of the platform to one or more designated parties.

In other embodiments, the standing desk may receive a signal from a sensor associated with the user of the standing desk. The sensor associated with the user may be active or passive sensors. The sensor associated with the user may be an radio frequency identification tag worn by the user and detected by a transmitter or sensor of the standing desk.

BRIEF DESCRIPTION OF THE DRAWINGS

Illustrated embodiments are described in detail below with reference to the attached drawing figures, which are incorporated by reference herein, and where.

DETAILED DESCRIPTION OF THE DISCLOSURE

The illustrative embodiments provide a system, method, and devices for providing biometrics relating to usage of a standing desk. One or more sensors may be utilized to determine when the user approaches the standing desk, the desired/preferred high, the position and/or orientation of the user, usage time for the standing desk, medical, physician specified, and other technical data of the standing desk, and other applicable information.

The position and orientation of the user may be determined utilizing one or more biometric sensors worn, positioned, or integrated on the body or clothing of the user. For example, Bluetooth low energy (BLE), radio frequency identification tags, or other short-range wireless signals or communications may be utilized between sensors and devices of the system. The system may utilize signal strength, location/proximity information, and other applicable information to make determinations. The system may also utilize one or more sets of user preferences associated with the standing desk and/or sensors to perform automated processes, data analysis, or other actions.

The data and information associated with the standing desk may be utilized by the user, medical professionals, businesses/organizations/entities/employers, or other applicable parties or individuals. For example, the information may be utilized to determine whether the standing desk is being fully or effectively utilized. The use of the standing desk may be utilized to ensure that the user is alternating positions and not sitting excessively for the well-being of the user.

The system may also utilize any number of alerts to provide the information and data determined by the system. The alerts may be communicated through wearable devices (e.g., smart watches, bands, straps, etc.), computing devices (e.g., desktop computers, laptops, smart televisions, etc.), wireless devices (e.g., smart phones, tablets, gaming devices, etc.), or other applicable systems, equipment, or devices proximate the user. In one embodiment, the system may provide a suggestion that the user transition to standing from sitting. The system may also provide statistics for one or more custom time periods, hours, work days, days, weeks, or years regarding utilization of the standing desk. In one embodiment, a mobile application or program may periodically display applicable information to the user regarding utilization of the standing desk, applicable statistics, alerts, and so forth. In some embodiments, employers or others may associate usage of the standing desk with achievable incentives for the user. As a result, the user may want (or be required to) track utilization of the standing desk. Any number of other incentives or motivations may be utilized (e.g., badges, awards, coupons, discounts, monies, tokens, etc.).

Although described as a standing desk herein, any number of movement or standing-based desks, furniture pieces, exercise equipment, or mechanisms may be utilized, such as treadmill desks, standing desk converters, biking desks, ellipticals, balance platforms, vibration platforms, exercise ball chairs, and so forth.

The illustrative embodiments may be utilized with fall detection and monitoring systems to provide additional data and information that may be beneficial to a user, medical professionals working with the user, the user's employer, or other relevant parties. Information such as height, weight, activity level, condition, medical issues, and age of a patient may be utilized to determine how much standing is appropriate for the user. Various thresholds may be utilized to determine how much standing is beneficial to the user and whether a potential fall is imminent, likely, or risks are elevated. Additional factors utilized to provide automated assessments may include physical condition, time of day, exercise/physical activity level, medication consumption, heart range changes, and other applicable information internal or external to the user. Additional information, data, and parameters utilized by the system may include age, height, weight, BMI, activity level, waist size, length of limbs, skin pore density, heart rate, respiration rate, blood pressure, arterial pressure, blood oxygenation, skin resistance, bone density, orientation with respect to center of gravity (e.g., resting and active), dominant hand, dominant foot, feet posture, and other medically relevant data. The biometrics measured from a user may be utilized to provide alerts regarding utilization or non-utilization of the standing desk.

The sensor may be worn by the user as clothing, a biosensor, or other wearable. As a result, the user does not have to focus on holding a device or ensuring a proper biometric interface. The sensor may represent a smart watch, bracelet, helmet, hearing aid, sticker, patch, band, smart clothing, implantable, or other smart wearable. The sensor may be worn on one or more of a wrist, ankle, belt, arm, chest, pocket, leg, hip, neck, or any number of positions associated with the body, jewelry, or articles of clothing. For example, the sensor may be worn, attached, adhered, slipped, or integrated into a pocket, sleeve, or other aspect of a user's body, clothing, or accessories. The sensor may be integrated with a shirt, hat, belt, shoe, bag, or other article of clothing or accessory worn or carried by the user. The biosensing wearable may be rechargeable and reusable or disposable/single-use.

Figure 1:
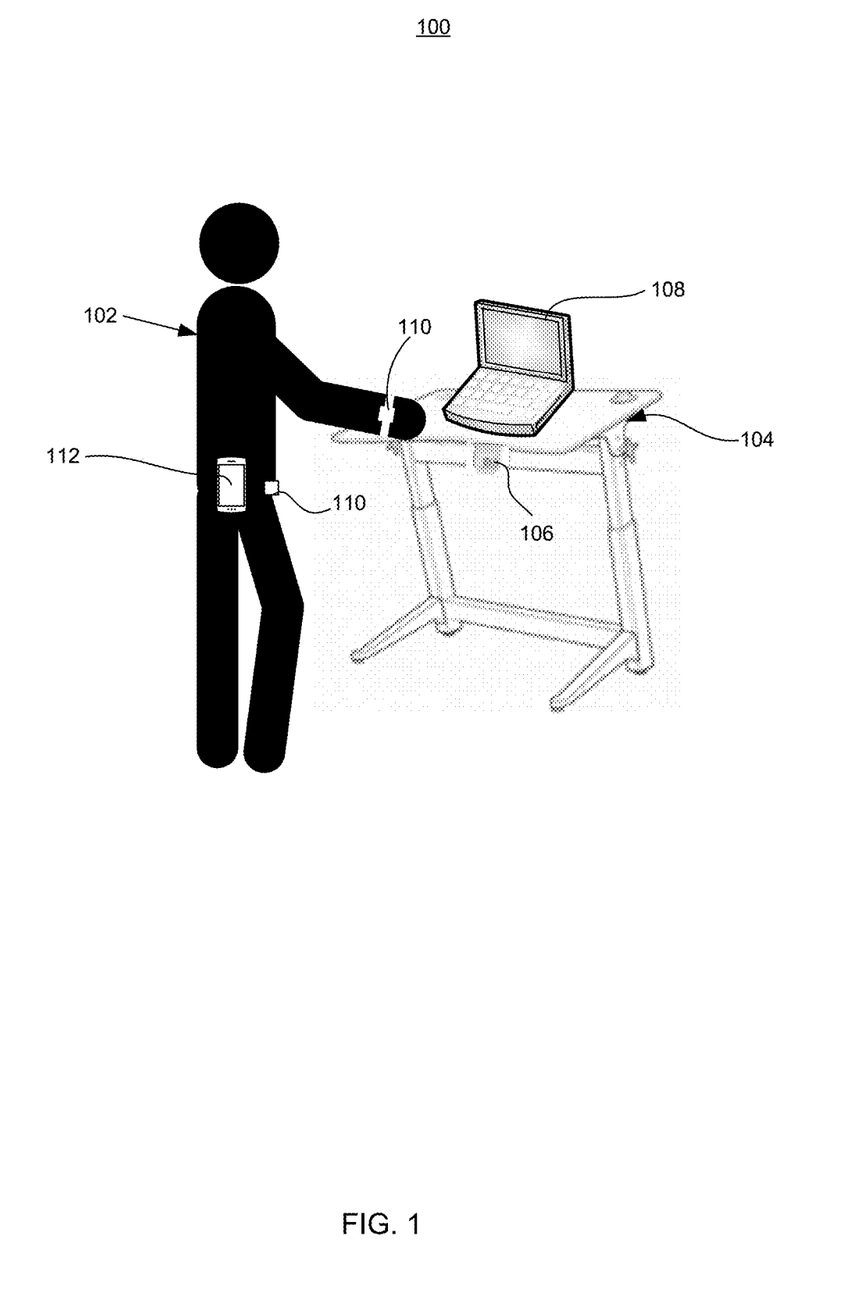
FIG. 1 is a pictorial representation of a standing desk environment in accordance with an illustrative embodiment.

FIG. 1 is a pictorial representation of a standing desk environment 100 in accordance with an illustrative embodiment. The standing desk environment 100 may represent any number of environments in which a user 102 may work, study, live, recreate, reside, use, or otherwise visit. The standing desk 104 may be specially configured to be raised and lowered for utilization by the user 102 or may be a traditional desk that is retrofitted with a standing desk converter, platform, or extensions. The user 102 may utilize a standing desk 104 including a sensor 106. The standing desk 104 may be manufactured with the sensor 106, integrated, or may be separately attached, interconnected, or integrated. For example, the sensor 106 may be powered by the power system(s) (e.g., power adapters, transformers, batteries, power ports, wiring, plugs, utilities, etc.) of the standing desk 104 that are utilized to raise, lower, or otherwise operate the standing desk 104. The standing desk 104 may be manufactured or retrofitted by any number of manufacturers (e.g., Varidesk, Flexispot, AirRise, Eureka, Vivo, Conquer, Symmetry, Adapt X, Innovative Winston, Changedesk, Luxor, Ergotech, ErgoDepot, ZooVaa, Uplift, Kangaroo, etc.). The standing desk 104 may support equipment, systems, devices, or so forth, such as a laptop 108 or other electric, or manual tools, systems, equipment, peripherals, and devices, monitors/displays/televisions, workstations, and working surfaces.

The user 102 may be wearing sensors 110. The sensors 110 may be worn on the body or clothing of the user 102. The sensors 110 may also be implanted, connected, adhered, worn, or otherwise integrated into or on the body of the user 102. The sensors 110 may represent active or passive devices. For example, the sensors 110 may represent and active device, such as a smart watch/band with at least a battery, transceiver(s), biometric sensors, and logic that both sent and receives wireless signals including applicable information or data. In another example, the sensors 110 may represent a passive device, such as a radio frequency identification (RFID) tag, that is activated in response to a wireless signal from the sensor 106 to communicate information or data.

In one embodiment the sensor 106 or sensors 110 (or other sensors in the standing desk environment 100 that are not shown) may determine the position and/or orientation of the user 102. In one embodiment, the sensor 106 may utilize an optical, vision, or imaging system or other sensors or groups of sensors to determine the position and orientation of the user 102. For example, the sensor 106 may determine the proximity of the user to the standing desk 104, the orientation of the body of the user (e.g., legs, torso, shoulders, arms, head, etc.), movements of the user (e.g., swaying, steps, etc.). As a result, the other sensors 110 may not be needed. In another embodiment, the laptop 108 may utilize an integrated camera and program to determine the position and orientation of the user. The position and orientation of the user may be determined constantly, in response to changes, at predetermined periods, in response to an activity, selection, or action, or based on other criteria.

The user 102 may also have a wireless device 112, such as a smart phone. The wireless device 112 may also be utilized as a sensor that communicates with the sensor 106 to indicate the position and orientation of the user 102. The sensor 106 may be configured to receive feedback from multiple devices/sensors simultaneously to provide more accurate information.

The sensor 106 may track how long the user 102 utilizes the standing desk 104. For example, the sensor may mark times that the user stands up or approaches the standing desk 104, sits down, or leaves the standing desk 104. As a result, utilization of the standing desk 104 is tracked to provide relevant information, data, statistics, and so forth.

As shown, the standing desk 104 may include components including, but not limited to, a working surface (usually horizontally positioned like the top of a desk), supports attached to the working surface, the supports may include motors, hydraulics, springs, counterbalances, or other movement mechanisms (e.g., pistons, linkages, rails, pulleys, belts, etc.) for raising and lowering the working surface, and one or more bases (e.g., frame, legs, horizontal extensions, etc.) for supporting the supports. All or portions of the supports may extend substantially vertically to position the working surface at the desired height and level. The standing desk 104 may utilize any number of sizes, shapes, or configurations (e.g., static standing desks, adjustable-mechanical, desk mounts, mobile desks, gas lift, electrical standing desk, standing desk converters, etc.).

Figure 2:
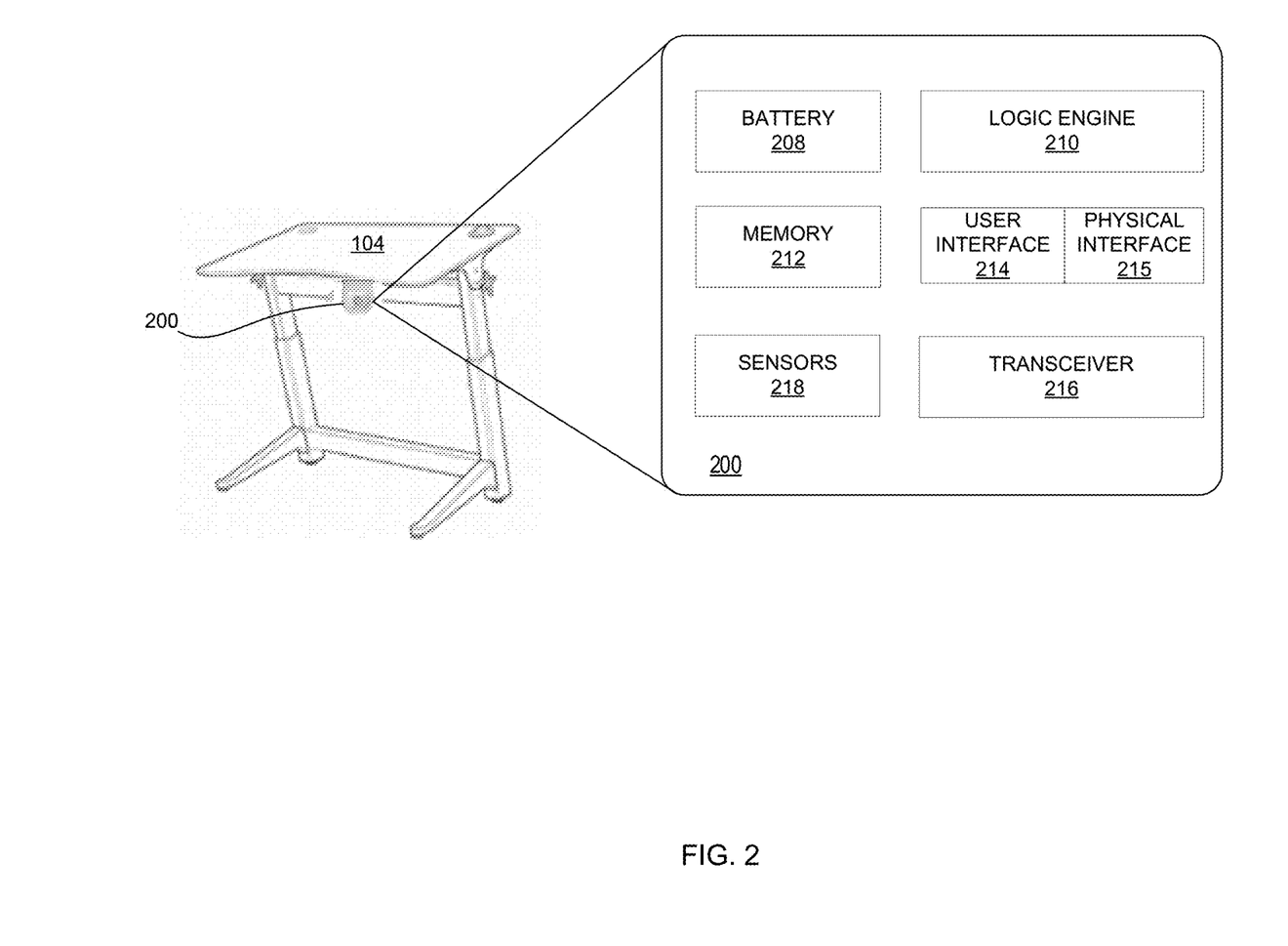
FIG. 2 is a pictorial representation of a sensor of a standing desk in accordance with an illustrative embodiment.

FIG. 2 is a block diagram of a sensor 200 of a standing desk in accordance with an illustrative embodiment. In one embodiment, the sensor 200 may be represented by sensor 106 of FIG. 1. In other embodiments, the sensor 104 may also represent the sensors 110 of FIG. 1. The sensor 200 may represent a standalone sensor that may be connected to the systems, wiring, or components of a standing desk. The sensor 200 may also represent an integrated portion of the standing desk. For example, the description of FIG. 2 may be relevant to the standing desk.

The sensor 200 may be wirelessly linked to any number of sensors, systems, or devices/wireless devices (not shown), such as the wireless device 112 of FIG. 1. For example, wireless devices may represent wearable devices, communications devices, computers, entertainment devices, or so forth. Sensor measurements, user input, selections, and commands may be received from either the sensor 200 or the wireless device for processing and implementation by the standing desk.

In some embodiments, the wireless device or other wearable devices may also act as a logging tool for sensor data or measurements made by the sensor 200. For example, the wireless device may receive and share usage data captured by the sensor 200 in real-time including user position, time standing, activity performed, environmental data, and so forth. As a result, the wireless device may be utilized to store, display, and synchronize sensor data received or measured by the sensor 200. In one example, the wireless device may store external command profiles for implementing various standing desk changes or adjustments, reporting or alert processes, or other processes, steps, applications, functions, or so forth. For example, the wireless device may display user pulse rate, temperature, proximity, location, blood oxygenation, distance, calories burned, and so forth as measured by the sensor. The wireless device may also store environmental measurements, spatial information, sound information, and other data regarding known or typical conditions (e.g., temperature, sounds sources, noise levels, environmental conditions, etc.) for specific locations that may be utilized to perform measurements or implementation of the user preferences, settings, and/or parameters. This same information and data may be stored in a memory 212 temporarily or permanently for utilization, logging, historical information, or any number of other uses or purposes. The sensor 200 may also store all of this information for immediate or subsequent access (e.g., archived information).

In one embodiment, the sensor 200 may include a battery 208, a logic engine 210, a memory 212, a user interface 214, a physical interface 215, a transceiver 216, and sensors 218. The sensor 200 and the wireless device may have any number of electrical configurations, shapes, and colors and may include various circuitry, connections, and other components utilized to perform the illustrative embodiments.

As previously noted, the sensor 200 may be integrated with, connected or attached to, or docked with the standing desk 104. The sensor 200 may also be configured to dock with the standing desk. In one embodiment, the sensor 200 may magnetically dock with electronics of the standing desk 104. For example, contacts, pins, connectors, or a part of the sensor 200 may interact with the standing desk 104. The sensor 200 may also represent a stand-alone device that may be attached to the standing desk 104.

In one embodiment, a power system (e.g., standard power plug/cord, transformer, converters, etc.) or a battery of the standing desk may power both the standing desk, associated electronics, and the sensor 200. Any number of standard power plugs or outlets may be incorporated into the standing desk 104.

The battery 208 is a power storage device configured to power the sensor 200. The battery 208 may power the sensor 200 even if the sensor 200 is not integrated with a hardwired power source. The battery 208 may also represent the power system of the sensor 200 that may include plugs, interfaces, transformers, amplifiers, converters, or so forth. In other embodiments, the battery 208 may represent a fuel cell, thermal electric generator, inductive power system, solar cell, ultra-capacitor, or other existing or developing power storage technologies. In other embodiments, the sensor 200 may not include batteries, but may instead only include a power system that is integrated with the standing desk 104.

The logic engine 210 is the logic that controls the operation and functionality of the sensor 200. The logic engine 210 may include circuitry, chips, and other digital logic. The logic engine 210 may also include programs, scripts, and instructions that may be implemented or executed to operate the logic engine 210. The logic engine 210 may represent hardware, software, firmware, or any combination thereof. In one embodiment, the logic engine 210 may include one or more processors. The logic engine 210 may also represent an application specific integrated circuit (ASIC) or field programmable gate array (FPGA). The logic engine 210 may utilize sensor measurements, user input, user preferences and settings, conditions, factors, and environmental conditions to determine the identity of the user, position, orientation, and usage information (e.g., coming and going information, position of the standing desk, etc.), at least in part, from measurements performed by the sensor 200. The sensor 200 may identify the user utilizing pre-specified devices, images, body composition, or so forth. The identity of the user may be utilized by the logic engine 210 to manage specific configuration of the sensors 218 (including the microphone array). For example, the logic engine 210 may detect information (e.g., identified boys) to set the applicable height and configuration of the standing desk 104. The standing desk 104 may be configured to adjust the height as well as the horizontal position of the working surface. For example, the working surface may be rotated, pivoted, or moved toward or away from the user utilizing one or more motors, belts, actuators, pistons, or so forth. The standing desk 104 may also be configured based on the activity of the user, such as writing by hand on the working surface, typing on a laptop, reading a book off of the working surface, or so forth.

In one embodiment, the logic engine may determine spatial information as well as self-configurations and other actions for the standing desk 104 and the sensor 200 based on measurements and data from the sensors 218 as well as other connected devices. In one embodiment, the logic engine 210 may manage the self-configuration based on measurements and data from the sensors 218 as well as other connected devices. The logic engine 210 may also perform any number of mathematical functions (e.g. determining body orientation, average rate of use of the standing desk 104 per hour, day, or year, etc.) to determine or infer the correct standing desk 104 and sensor 200 configuration, sensor sensitivity, biasing, or adjustments that may be required. The logic engine 210 may also determine messages that should or need to be communicated to the user regarding utilization or non-utilization of the standing desk 104, such as encouragement, usage statistics, posture information, standing desk 104 configurations, and so forth.

The logic engine 210 may utilize wireless signals from other sensors/devices, historical measurements, trends, component degradation or failures, time, and other sensor measurements as causal forces to enhance a mathematical function utilized to perform the determinations, presentation, processing, calculations, and extrapolations performed by the logic engine 210. As previously noted, the sensor 200 may detect active or passive signals to detect the presence, position, location, and other applicable information relevant to the user and the user's utilization of the standing desk 104. For example, the transceiver 216 may communicate a powered signal that is reflected back by a sensor or device worn by the user to provide relevant information.

The logic engine 210 may also process one or more of automated instructions, programs, user preferences, and user input to determine how spatial information is communicated/displayed, utilized, and otherwise implemented by the sensor 200. Specific configuration commands or activities may be allowed based on sensor measurements, events, environmental conditions, proximity thresholds, locations, and so forth. For example, the logic engine 210 may implement a spatial information macro allowing the user to view the accrual of biometric information relating to utilization of the standing desk 104 in real-time or per specified time period. The logic engine 210 may utilize other biometrics, such as exercise, blood pressure, temperature, respiration rate, pulse rate, doctor recommendations, posture/stance, and other applicable information to recommend how much the user should utilize the standing desk 104 per given day or time period.

In one example, the spatial information is presented audibly for the user to receive information and make selections. For example, in response to the user approaching the standing desk 104, the sensor 200 may play an audible message indicating "configuring the desk for Dr. Selvam" and position the standing desk 104 accordingly. The sensor 200 or the standing desk number 104 may include a speaker for communicating information, data, and alerts. For example, the speaker may play a message from the logic engine 210 indicating "you have used the standing desk for 45 minutes today." The sensor 200 may also pose a question to the user, such as "have you fallen?" The information provided by the user may be utilized to send any number of alerts or messages regarding the status of the user. The logic engine 210 may help configure the standing desk 104 (and associated electronics) for one of many potential users that may use the standing desk 140 on a given day. As a result, the standing desk 104 may be used as a shared resource encourage people to both move and stand.

In one embodiment, a processor included in the logic engine 210 is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, performing mathematical calculations, and performing other related tasks.

The memory 212 is a hardware element, device, or recording media configured to store data or instructions for subsequent retrieval or access at a later time. The memory 212 may represent static or dynamic memory. The memory 212 may include a hard disk, random access memory, cache, removable media drive, mass storage, or configuration suitable as storage for data, instructions, and information. In one embodiment, the memory 212 and the logic engine 210 may be integrated. The memory 212 may use any type of volatile or non-volatile storage techniques and mediums. The memory 212 may store information related to the user, sensor 200, standing desk 104, wireless devices, and other peripherals, such as a wireless devices, RFID tags, smart glasses, smart watch, smart clothing, and so forth. In one embodiment, the memory 212 may display or communicate instructions, programs, drivers, or an operating system for controlling the user interface 214 including one or more displays, speakers, tactile generators (e.g., vibrator), and so forth. The memory 212 may also store user profiles, biometric readings, applications, historical location, position, orientation, and sound information, user input required for self-configuration processes, configuration data (e.g., default, standard, baseline, factory programmed, etc.), user settings and preferences, thresholds, conditions, parameters, signal or processing activity, proximity data, and so forth.

The transceiver 216 is a component comprising both a transmitter and receiver which may be combined and share common circuitry on a single housing. The transceiver 216 may communicate utilizing low frequency (LF), high frequency (HF), or ultra-high frequency (UHF) radio frequency identification (RFID), near field communications (NFC), near-field magnetic induction (NFMI) communication, Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. For example, the transceiver 216 may coordinate communications and actions between the sensor 200 and one or more devices, tags, or sensors utilizing radio frequency communications. The transceiver 216 may also be a hybrid transceiver that supports a number of different communications. The transceiver 216 may also detect time receipt differentials, amplitudes, and other information to calculate/infer distance between the sensor 200 and external devices, such as tags, smart watches, wireless device or other sensors. The transceiver 216 may also represent one or more separate receivers and/or transmitters.

The components of the sensor 200 may be electrically connected utilizing any number of wires, contact points, leads, busses, chips, wireless interfaces, or so forth. In addition, the sensor 200 may include any number of computing and communications components, devices or elements which may include busses, motherboards, circuits, chips, sensors, ports, interfaces, cards, converters, adapters, connections, transceivers, displays, antennas, and other similar components.

The physical interface 215 is hardware interface of the sensor 200 for connecting and communicating with computing devices (e.g., desktops, laptops, tablets, gaming devices, etc.), wireless devices or other electrical components, devices, or systems. In one embodiment, the physical interface 215 may include power, communications, wireless, and other ports and interfaces. For example, synching and charging may be performed by an external device through the physical interface 215.

The physical interface 215 may include any number of pins, arms, or connectors for electrically interfacing with the contacts or other interface components of external devices or other charging or synchronization devices. For example, the physical interface 215 may include USB, HDMI, Firewire, micro USB, and AC/DC ports and interfaces. In one embodiment, the physical interface 215 is a magnetic interface that automatically couples to contacts or an interface of the standing desk 104. For example, the physical interface 215 may magnetically connect to an exterior surface of the sensor 200. In another embodiment, the physical interface 215 may include a wireless inductor for powering the sensor 200 without a physical connection to the standing desk 104.

The user interface 214 is a hardware and software interface for receiving commands, instructions, or input through touch (haptics) of the user, voice commands, or predefined motions. For example, the user interface 214 may include a touch screen (including a fingerprint scanner), one or more cameras or image sensors, microphones, speakers, and so forth. Although not shown, the one or more speakers may include a number of speaker components (e.g., signal generators, amplifiers, drivers, and other circuitry) configured to generate sounds waves at distinct frequency ranges (e.g., bass, woofer, tweeter, midrange, etc.) or to vibrate at specified frequencies to be perceived by the user as sound waves.

The user interface 214 may be utilized to control the other functions of the sensor 200. The user interface 214 may include the hardware buttons, one or more touch sensitive buttons or portions, a miniature screen or display, or other input/output components. The user interface 214 may be controlled by the user or based on commands received from the standing desk 104, wireless device, or other authorized devices. The user may also establish or cancel self-configuration of the sensor 200 utilizing the user interface 214.

The one or more microphones of the user interface 214 may represent any number microphone types utilized to sense the user's voice, external noise, and so forth. The microphones may be utilized to receive user input as well as detect the presence of the users (the microphones may also be part of the sensors 218).

The user interface 214 may include any number and type of devices for receiving user input and providing information to the user. In one example, the device includes a tactile interface, an audio interface, and a visual interface. The tactile interface includes features that receive and transmit via touch. For example, as noted above, the sensor may include one or more buttons to receive user input. In one example, a single button of the sensor 200 may identify the user utilizing a fingerprint scan as well as recording a time that the user began using the standing desk 104. Another selection of the button may indicate that the user is leaving the standing desk 104. Buttons on the sensor may also control the configuration of the standing desk 104 moving between multiple positions (e.g., sitting, sitting on a bar stool, standing, etc.) for one or more users and associate activities/actions performed by the one or more users.

The tactile interface portion of the user interface 214 may include momentum or orientation detecting devices to receive input via physical interactions with the standing desk 104. For example, accelerometers may be used to detect deliberate or unintended movements (e.g., swaying toward the desk, hitting the desk during a fall, etc.).

The tactile interface may also include one or more tactile output devices, such as haptic feedback devices. For example, the user may tap the standing desk 104 to indicate that it is in use or the user is leaving for tracking utilization. A motorized actuator with an offset weight may be provided inside the sensor to acknowledge tactile input and feedback.

The audio interface portion of the user interface 214 may include any suitable speaker and/or microphone, as known in the art. For example, a speaker may be as part of the housing of the sensor 200 and programmed to emit information in the form of audio output. Such output may include audible alerts regarding usage of the standing desk 104, suggestions for utilization or non-utilization of the standing desk 104, milestones, thresholds, or other applicable information or alerts. The microphone may also receive input from the user if the user has fallen.

In one embodiment, the biometric, private, and other secured data of the user may be encrypted and stored within a secure portion of the memory 212 to prevent unwanted access or hacking. The sensor 200 may also store important user profile and biometric data, such as medical information (e.g., medical conditions, logged biometrics, contacts, etc.) and identifying biometric information, for sharing in response to an emergency or authenticated request.

The sensors 218 may include photodetectors, miniature cameras, microphones, accelerometers, gyroscopes, impact/force detectors, thermometers, inertial sensors, thermal imaging devices, radar, and other similar instruments for detecting the user's status, position, orientation, motion, and environmental conditions. The sensors 218 may also be utilized to determine the biometrics, activities, locations, other users in the environment, animals, devices, and so forth. In one embodiment, the sensors 218 may store data that may be shared with other components (e.g., logic engine 210 implementing a configuration process), users, and devices. For example, the sensors 218 may detect when the user is standing completely upright, leaning forward slightly, knees straight, knees bent, arm position, head position, and so forth. The sensors 218 may also detect the proximity of the user to the sensor 200.

The sensors 218 may also include photodetectors, ultrasonic mapping devices, or radar that scan the body and body parts of the user when positioned for utilization. The mapping may also extend to the environment of the user. The topographical image may also be utilized to perform configuration of the standing desk 104 based on the determined position, orientation, activities/actions, and determinations of the sensors 218 with respect to the user and the standing desk 104.

The sensors 218 may pass measurements, readings, and data about the user and environment to the logic engine 210 for performing configuration processes and algorithms. Likewise, the memory 212 may store the location detection, sound processing and configuration programs, algorithms, steps, baseline data, sensor measurement data, and so forth. This data and information may also be communicated to a connected device for storage or analysis. The sensor measurements may be compared against the baseline data to determine variations and how to compensate or adjust the sensor 200 based on the sensor 218 measurements. The logic engine 210 may also perform pattern analysis with the sensor measurements to calibrate or tune the sensors 218 based on established patterns, historical data, or information.

Externally connected tags, chips, sensors, or wireless devices may include components similar in structure and functionality to those shown for the sensor 200. For example, a wireless device may include any number of processors, batteries, memories, busses, motherboards, chips, transceivers, peripherals, sensors, displays, cards, ports, adapters, interconnects, sensors, and so forth. In one embodiment, the wireless device may include one or more processors and memories for storing instructions. The instructions may be executed as part of an operating system, application, browser, or so forth to implement the features herein described. For example, the user may set preferences for the sensor 200 to communication information, perform processes, and self-configure based on specified events, locations, activities, or user input. Likewise, the preferences may manage the actions taken by the sensor 200 in response to identifying specific users are utilizing the sensor 200. For example, a height of the standing desk 104 may be distinct for a first user as compared to a second user.

The sensor 200 may also execute an application with settings or conditions for communication, self-configuration, updating, synchronizing, sharing, saving, identifying, calibrating, and utilizing biometric and environmental information as herein described. For example, alerts may be sent to the user to use the standing desk 104 (or transition the standing desk 104 from a sitting mode or configuration to a standing mode or configuration) in response to the user sitting for an hour of time. The alert may be communicated through a text message, in-application message communicated through the user's computer, smart phone, smart watch, or other device, audio alert from the user interface 214, vibration, flashing lights, display, or other system for the sensor 200 or standing desk 104. In another example, the sensor 200 may provide a warning if the user is swaying or may fall. Likewise, alerts may be sent to predetermined parties if the user does fall. In some embodiments, the sensor 200 may be attached to a walker, furniture, cabinets, or other devices for determining that the user is moving about a home, apartment, care facility, office, or other location. For example, the user may wear an RFID tag that may be detected as the user moves throughout a location as well as any potential fall events. In one embodiment, the sensor 200 may detect unexpected separations from an RFID tag to determine a fall event has happened. For example, the detected range between the two devices may suddenly change from two feet to four feet with the RFID tag well below the sensor 200 indicating an unwanted event has happened.

As originally packaged, the sensor 200 or the standing desk 104 may include peripheral devices such as charging cords, power adapters, inductive charging adapters, solar cells, batteries, lanyards, additional light arrays, speakers, smart case covers, transceivers (e.g., Wi-Fi, cellular, etc.), or so forth.

Figure 3:
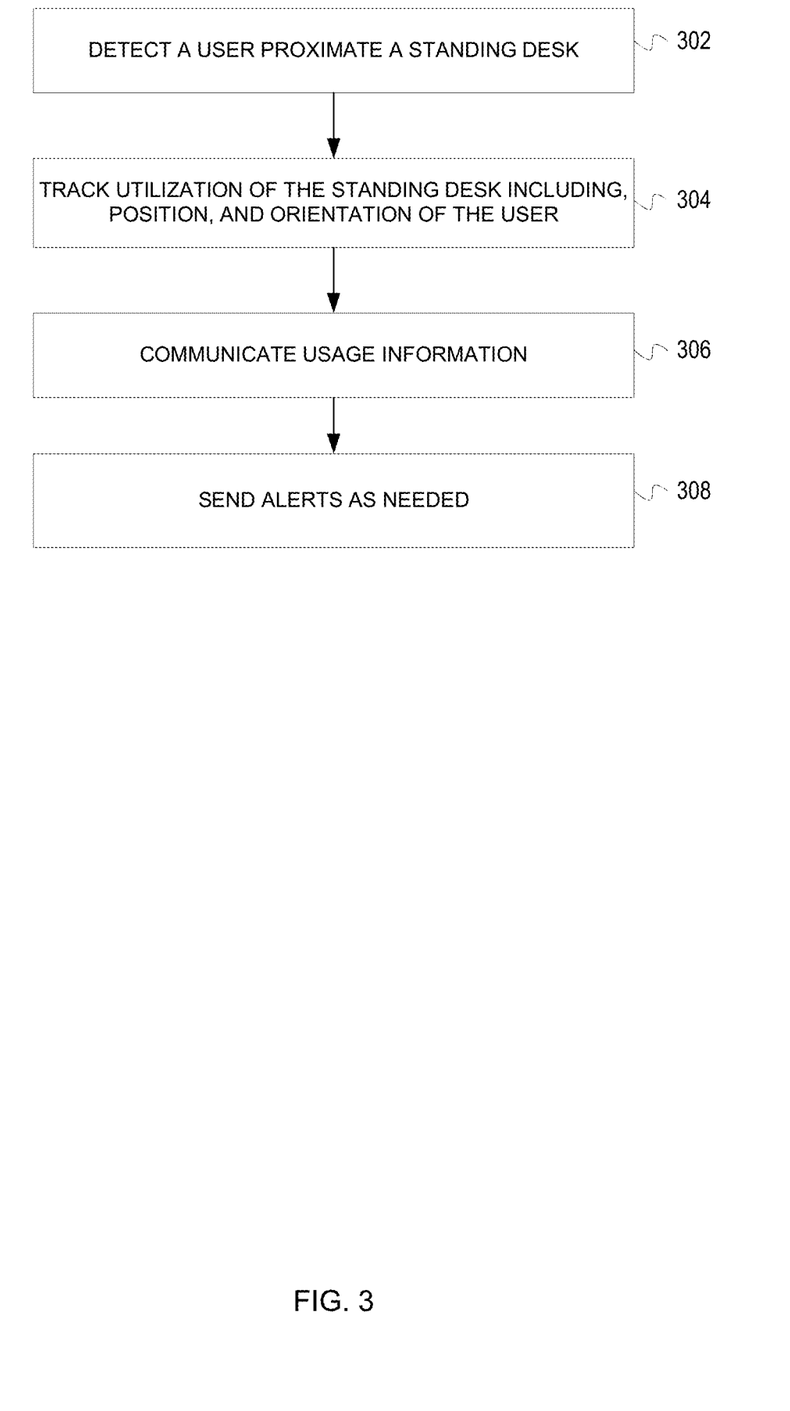
FIG. 3 is a flowchart of a process for detecting utilization of a standing desk in accordance with illustrative embodiments.

FIG. 3 is a flowchart of a process for detecting utilization of a standing desk in accordance with illustrative embodiments. The process of FIGS. 3-5 may be implemented by a standing desk system, standing desk, or sensor, such as those illustrated in FIGS. 1-2. For example, a standing desk may include one or more sensors that detect a user and/or sensors associated with the user to determine usage information including duration, position/orientation, and so forth. As previously noted, the standing desk may represent any number or configurations of standing desks or traditional desks converted or retrofitted to act as a standing desk. The standing desk may also represent other tools or devices that encourage motion or changes in activity.

In one embodiment, the process of FIG. 3 may begin by detecting a user proximate a standing desk (step 302). In one embodiment, a time and date may be associated with the user approaching the standing desk. Step 302 may also include determining that the standing desk has transitioned from a sitting mode to a standing mode. In one embodiment, a sensor of the standing desk may identify the user utilizing one or more optical, infrared, motion, proximity, or other sensors that may act independently. In another embodiment, the user may wear (on their body or clothing) any number of sensors that are detected by a sensor of the standing desk. The sensors may also be implanted in the user (e.g., pacemaker, identification chip, medical device, etc.). The sensors worn by the user may represent any number of actively powered or passively powered devices. For example, the sensor may be a smart watch worn by a user. In another example, the sensor may be an RFID tag integrated with a cell phone, belt, or shoes worn by the user (e.g., RFID sticker, label, etc.).

In another example, the smart phone or another wireless device commonly carried by the user may be used as the sensor. Step 302 may be utilized to determine when the user starts and stops using the standing desk. The user may also be detected utilizing capacitive sensors or accelerometers that detect the standing desk has been touched or moved. The user may also be detected utilizing a device, such as an RFID tag, smart watch, smart clothing, cell phone, or other applicable device. Active or passive communication or detection of signals may be performed.

Next, the standing desk system tracks utilization of the standing desk including position, and orientation of the user (step 304). The position and orientation of the user may be determined only utilizing sensors of the standing desk or sensors worn by the user. The position and orientation of the user may include the user's posture, leg position and stance, upper body inclination, shoulder position (e.g., shoulders back hunching, etc.), arm/elbow/hand position. The standing desk system may utilize time stamps to determine when the user approaches the standing desk or leaves the standing desk. The standing desk system may also track the configuration of the standing desk, such as a sitting mode and standing mode. The standing desk system may also track biometrics associated with the user as part of the process of step 304. The biometrics may be utilized to determine if the user is safe in using the standing desk. For example, the standing desk system may determine if the user is becoming unstable or their biometrics indicate that the user should sit down or otherwise rest. The standing desk system may also track the posture of the user to ensure that proper posture is being utilized for the well-being of the user's back. Infrared sensors, radar sensors, or integrated microphones may also detect and identify the user. The standing desk may also record the activities performed at the standing desk and associated configurations of the standing desk, such as height of the working space, tilt/incline of the working space, and so forth. The configuration and reconfiguration data recorded by the standing desk and associated sensors may be utilized to customize the configuration or reconfiguration of the standing desk in the future. For example, when the user transitions from typing, to writing by hand, or reading from content on the standing desk different height levels may be automatically implemented to move the working space (e.g., top of the desk).

Next, the standing desk system communicates usage information (step 306). The usage information may include reports or statistics regarding utilization of the standing desk by one or more users. The usage information may also include suggestions for the one or more users to utilize the standing desk or a "standing mode" of the standing desk. For example, the user may receive a message that says, "why don't you stand at your desk?" The standing desk system may also provide encouraging messages, such as "you are hallway to your goal of standing at your desk for two hours a day." Any number of thresholds, settings, or parameters may be utilized as provided by the user, an entity, health professionals, or so forth. The usage information may also specify feedback for better using the standing desk, such as "consider standing closer to the standing desk", "you can improve your posture by holding your shoulders back", and other information that may be presented based on the utilization information.

Next, the standing desk system sends alerts as needed (step 308). The alerts may provide information to the user and one or more designated users/devices. For example, the alert may specify that the user should stand or sit for the well-being of the user. The condition or status of the user may indicate when sitting or standing is most appropriate while avoiding any negative health events or conditions. In one embodiment, the alerts may be sent based on the biometrics of the user as read by the standing desk system, user wearables, wireless devices, or so forth. The alerts may also include an alert that the user has or is falling. The alert may also suggest that the user use or stop using the standing desk. The alert may also give posture, location, and orientation alerts, such as "move closer to the standing desk and straighten your back for maximum health benefits." In one embodiment, the alerts may be presented at any time. The alerts may be communicated through text message, email, in-application message, phone call, or other digital mediums. Alerts may also be communicated audibly through the standing desk or other systems, equipment, or devices (e.g., speaker/intercom systems).

Figure 4:
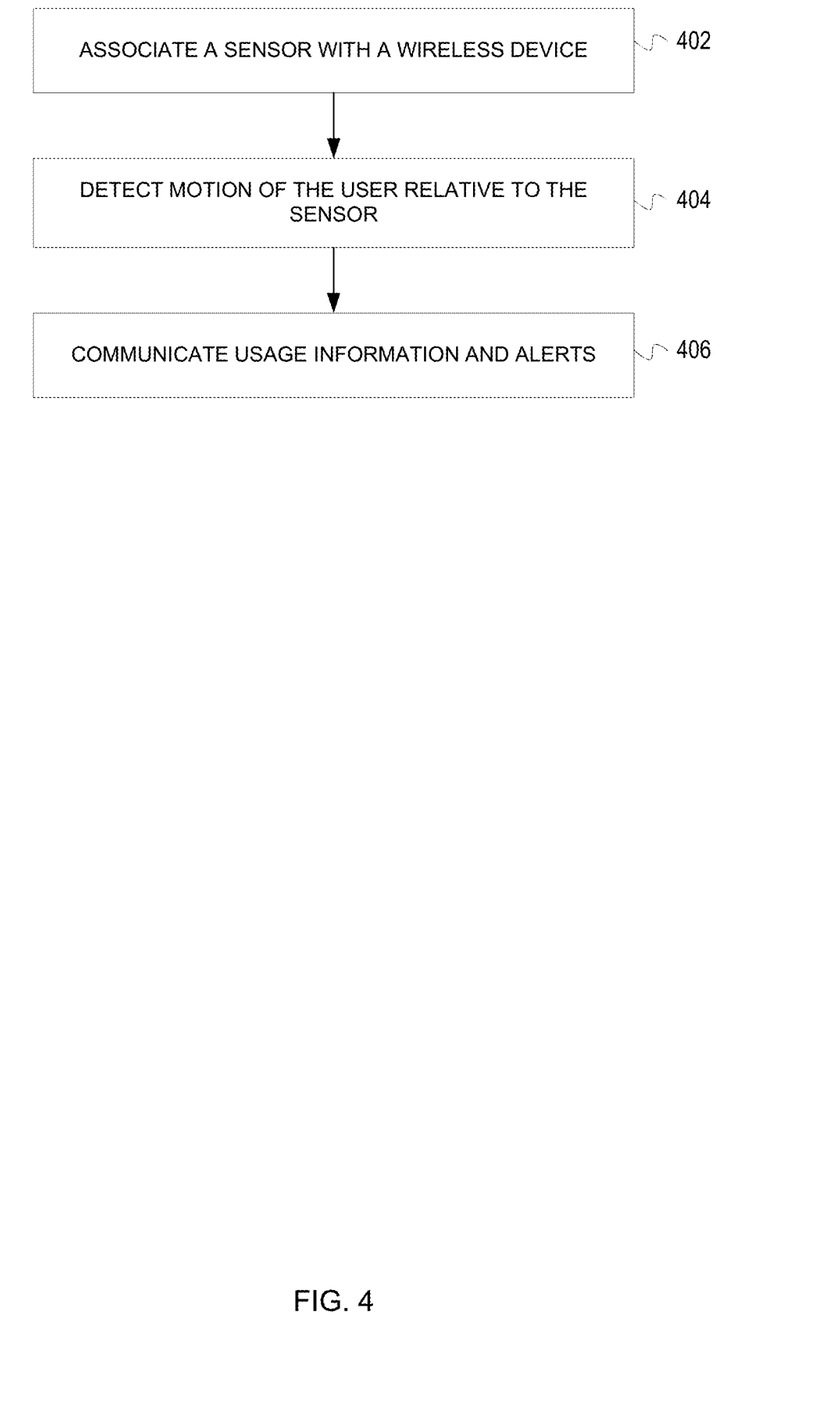
FIG. 4 is a flowchart of a process for tracking utilization of a standing desk in accordance with illustrative embodiments.

FIG. 4 is a flowchart of a process for tracking utilization of a standing desk in accordance with illustrative embodiments. The process of FIG. 4 may be integrated with or separate from the processes of FIGS. 3, 5. In one embodiment, the process may begin by associating a sensor with a wireless device (step 402). The sensor may be removably attached to any number of devices, such as a standing desk, walker, stool, shower stall, bar, cabinets, or so forth. The wireless device may represent another sensor, tag, smart phone, smart watch, or other device that communicates with the sensor (actively or passively). In one embodiment, the sensor may be paired or registered with the wireless device. Any number of wireless signals, protocols, or standards may be utilized (e.g., Bluetooth low energy, Wi-Fi, RFID signals, etc.). A user interface may be utilized to associated different devices with a user.

Next, the sensor detects motion of the user relative to the sensor (step 404). The sensor may measure the motion of the user as he/she approaches the sensor, sways, moves slightly, or so forth. For example, the sensor may be attached to a standing desk and may record when the user is standing at the standing desk and for how long. In another example, the sensor may be attached to a walker and may record when and how the walker is utilized including various movements of the user. The sensor may also detect if the user falls while proximate the sensor. The sensor may be temporarily or permanently attached to furniture, mobility components, or other devices. The sensor may be attached utilizing straps, adhesives, tabs, Velcro, buttons, mounts, an interference fit, or other attachment mechanisms.

Next, the sensor communicates usage information and alerts (step 406). The information and alerts may be communicated to the user and/or any number of specified devices/users. The usage information may be communicated based on any number of thresholds. The alerts may indicate if the user has fallen, not moved within a specified time period, or based on other biometrics measured by the sensor or other associated sensors (e.g., the wireless device).

The wireless device may represent one or more biosensing wearable devices (e.g., helmets, hearing aids, stickers, bands, sensor packages, hearables, etc.), smart phones, web interfaces, or so forth. For example, the microphones, speakers, accelerometers, timers, and other components of the biosensing wearable may be utilized to determine biometric information. The process of FIG. 4 may be performed automatically or utilizing user input, interactions, or feedback. The sensor may utilize physiological parameters to determine how much utilization of the standing desk or device is appropriate. The user physiology may include height, weight, activity, body dimensions, symmetry, and size, dominant hand, and age of a patient. The physiological parameters may be determined from user input, application utilization, measurements, data from the wireless device, a user profile, medical information, or so forth.

Figure 5:
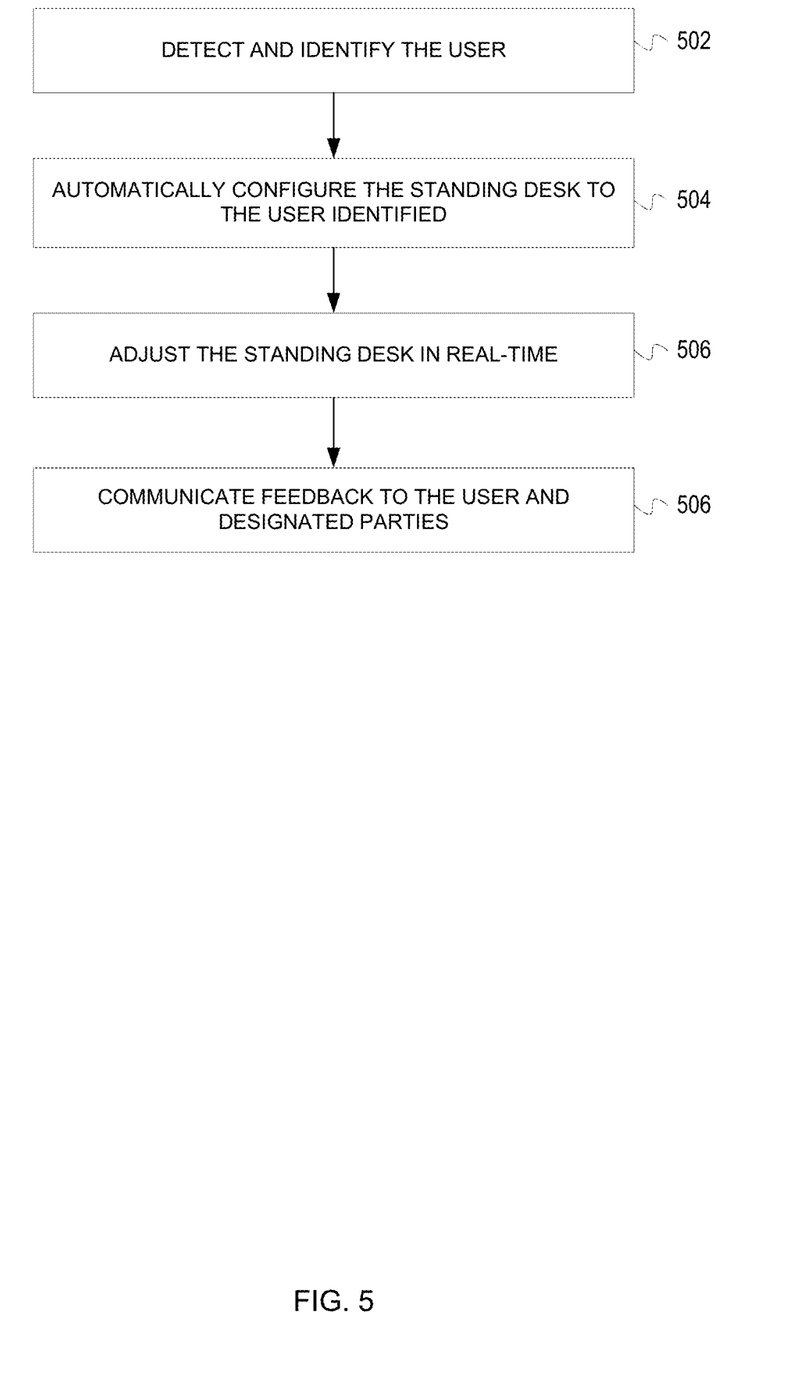
FIG. 5 is a flowchart of a process for utilizing a standing desk in accordance with an illustrative embodiment.

FIG. 5 is a flowchart of a process for utilizing a standing desk in accordance with an illustrative embodiment. The process of FIG. 5 may be integrated with or separate from the processes of FIGS. 3-4. The process of FIG. 5 may begin by detecting and identifying the user (step 502). The user may be identified utilizing the sensors of the standing desk system and/or sensors/devices worn, carried, or integrated with the user. Numerous users may utilize a single standing desk. As a result, it is important for the standing desk system to identify one of potential users. A timestamp may be recorded for each time the user approaches or leaves the standing desk to provide accurate usage results. The relevant information may be compiled with other user sensor/biometric devices to provide an accurate measurement of standing or movement of the user throughout the day.

Next, the standing desk automatically configures the standing desk to the user identified (step 504). The standing desk may store user preferences for a number of users. The standing desk may automatically configure the height, tilt, horizontal extension, power, mode, and other configurable portions of the standing desk. For example, an associated electronic device or computer utilized with the standing desk may be automatically logged in for the user or prepared to receive other information (e.g., password, pin, biometrics, etc.). The standing desk may even determine an activity being performed by the user to specially configure the standing desk. For example, a higher height may be utilized when reading than when the user is reading or typing. The user may program different settings for the standing desk and the standing desk may learn them over time utilizing machine learning or artificial intelligence.

Next, the standing desk adjusts itself in real-time (step 506). The standing desk may reconfigure itself based on the biometrics, activities, time-of-day or other factors. At any time, the standing desk may reconfigure itself to best suit the needs and wants of the user. The standing desk may utilize a sensor to generate a signal that is reflected of off the user to identify the user in step 502 as well as determine other applicable usage information, such as proximity to the desk/position, posture/orientation, activity/actions being performed, and so forth.

Next, the standing desk communicates feedback to the user and designated parties (step 508). The user may communicate the user's biometrics, time using the standing desk (e.g., standing, sitting, etc.), information on the posture of the user, and other information. The communications of step 508 may include feedback or suggestions to best improve the health of the user, such as time to meet a usage goal, posture/stance instructions, encourage the user to lift one knee at a time to stimulate blood flow, and so forth. The standing desk may provide reminders, warnings, or alerts for the user to stand, sit, or even walk away for a moment. In one embodiment, the standing desk may utilized information from the user's doctor to implement a program for standing and sitting. The standing desk system herein described may be utilized to avoid or treat the negative effects of extensive sitting. In particular, the standing desk may help users avoid or treat potential blood clots, circulation issues, muscle atrophy, deep vein thrombosis, weight gain, anxiety, back problems, varicose veins, osteoporosis, body image problems, heart disease, diabetes, cancer, and mental health issues. The illustrative embodiments may be utilized to specifically address health issues cause from excessive sitting.

The sensor may perform a calibration process for the sensors. The calibration may be performed based on historical information, bias levels, and so forth. The calibration process may also include a reboot or reset. Various thresholds may be utilized to perform fall risk prediction and detection. In one embodiment, the sensors may communicate an alert indicating that fall likelihood has surpassed one or more levels, percentages, or so forth. In another embodiment, the system may communicate one or more alerts indicating that a fall has happened to one or more specified users, devices, systems, applications, or so forth.

The standing desk of the illustrative embodiments is configured to detect, analyze, and alert the user and others regarding utilization or non-utilization of the standing desk.

The standing desk may detect standard wearable and wireless devices (e.g., smart watches, bands, smart clothing, jewelry, smart phones, etc.). The standing desk may also detect active or passive sensors. The standing desk may also include sensors, such as optical, infrared, laser, proximity, and other available sensors, to detect the user and utilization of the standing including position, orientation, movements, and so forth. The captured information and data may be analyzed, processed, displayed, and communicated to the user and other applicable parties. The utilization information of the standing desk may be reported through in-app, browser, emails, text messages, or other applicable messages.

The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object-oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

Figure 6:
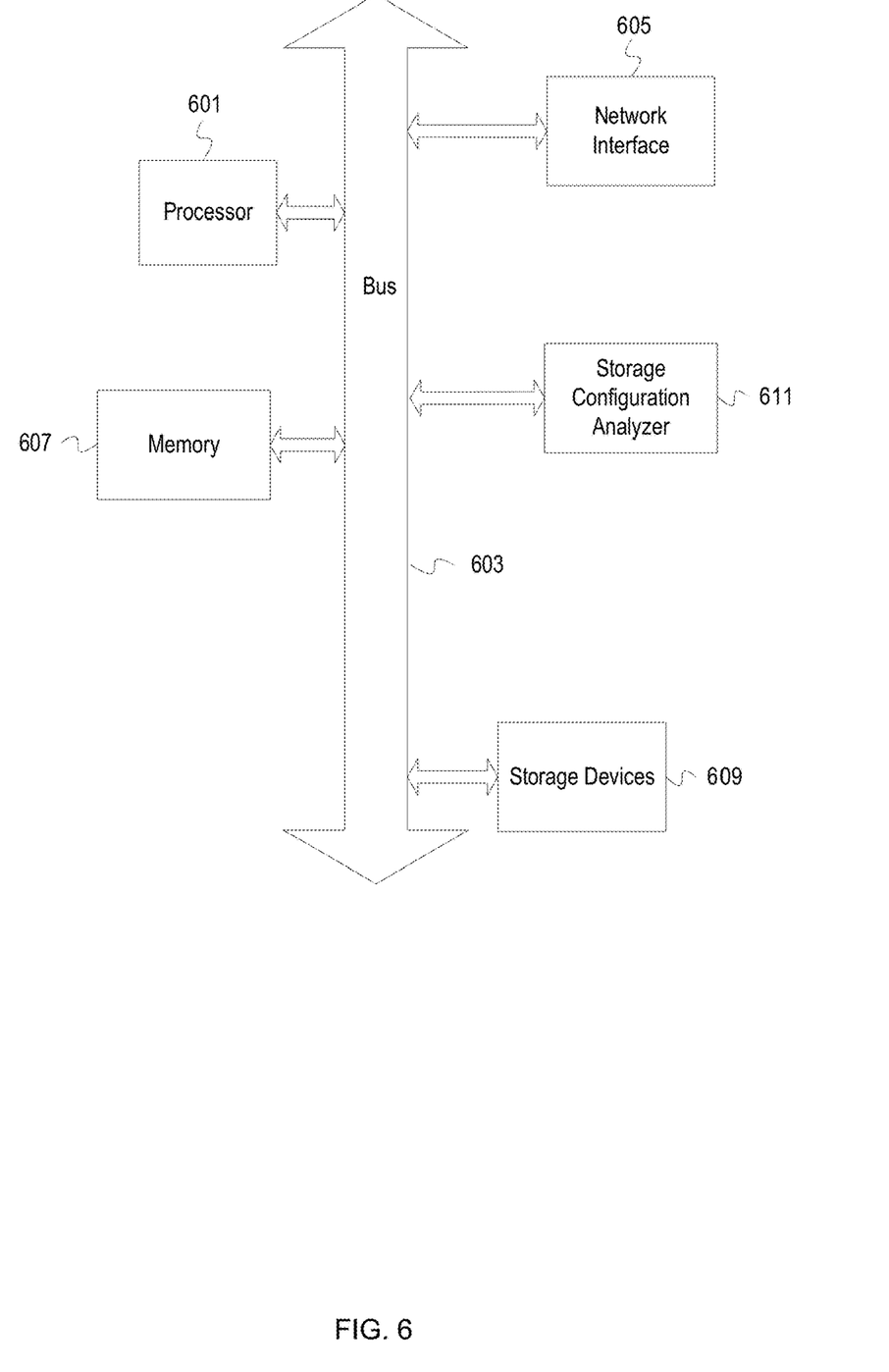
FIG. 6 depicts a computing system in accordance with an illustrative embodiment.

The illustrative embodiments may be implemented by an independent cloud system or network or any number of smart devices (e.g., centralized computers, servers, application networks, etc.). Historical information across patients, facilities, and organizations may be processed without identifying information to better perform analysis, predictions, assign values, calculate scores, establish thresholds for detecting falls and other unwanted patient events, and share data. FIG. 6 depicts a computing system 600 in accordance with an illustrative embodiment. The computing system 600 may be representative of all or portions of the standing desk of FIGS. 1 and 2. For example, the computing system 600 may represent a smart standing desk or retrofitted standing desk as described herein. The computing system 600 includes a processor unit 601 (possibly including multiple processors, multiple cores, multiple nodes, and/or implementing multi-threading, etc.). The computing system includes memory 607. The memory 607 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 603 (e.g., PCI, ISA, PCI-Express, HyperTransport®, InfiniBand®, NuBus, etc.), a network interface 605 (e.g., an ATM interface, an Ethernet interface, a Frame Relay interface, SONET interface, wireless interface, etc.), and a storage device(s) 609 (e.g., optical storage, magnetic storage, etc.). The system memory 607 embodies functionality to implement embodiments described above. The system memory 607 may include one or more functionalities that store personal data, parameters, application, user profiles, and so forth. Code may be implemented in any of the other devices of the computing system 600. Any one of these functionalities may be partially (or entirely) implemented in hardware and/or on the processing unit 601. For example, the functionality may be implemented with an application specific integrated circuit, in logic implemented in the processing unit 601, in a co-processor on a peripheral device or card, etc. Further, realizations may include fewer or additional components not illustrated in FIG. 6 (e.g., video cards, audio cards, additional network interfaces, peripheral devices, etc.). The processor unit 601, the storage device(s) 609, and the network interface 605 are coupled to the bus 603. Although illustrated as being coupled to the bus 603, the memory 607 may be coupled to the processor unit 601.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method for tracking utilization of a standing desk, comprising:
   detecting a user proximate a standing desk, wherein at least a wearable device worn by the user is detected by one or more sensors integrated with the standing desk;
   identifying the user utilizing the wearable device worn by the user;
   determining a position and an orientation of the user utilizing at least the one or more sensors of the standing desk, the orientation further indicates the posture of the user; and
   detecting time periods associated with the position and the orientation of the user utilizing the one or more sensors of the standing desk.

2. The method of claim 1, wherein the detecting comprises:
   receiving a signal from the wearable device associated with the user utilizing the one or more sensors.

3. The method of claim 1, wherein the detecting comprises:
   generating an optical signal utilizing the one or more sensors on the standing desk; and
   receiving a reflected signal detecting the user.

4. The method of claim 3, wherein the reflected signal further indicates the position and the orientation of the user.

5. The method of claim 1, wherein the time periods include timestamps for each plurality of positions and orientations of the user.

6. The method of claim 1, further comprising communicating an alert regarding utilization or non-utilization of the standing desk.

7. The method of claim 6, wherein the alert includes statistics for the user.

8. The method of claim 1, wherein the standing desk is configured to detect and identify a plurality of users.

9. The method of claim 1, wherein the standing desk detects one or more of the wearable device, a wireless device, and a standalone sensor.

10. The sensor of claim 1, wherein the platform is a standing desk or walk assistance device.

11. The sensor of claim 1, wherein the user is detected and identified utilizing one or more optical sensors.

12. The sensor of claim 1, further comprising:
    a transceiver configured to communicate with one or more devices worn by the user.

13. The sensor of claim 1, wherein the logic engine communicates an alert to the one or more designated parties.

14. The sensor of claim 1, wherein the alert indicates that a falling event has occurred.

15. The sensor of claim 1, wherein the logic engine further determines a position and an orientation of the user, and detects time periods associated with the position and the orientation.

16. The sensor of claim 1, wherein the sensor is attached to one or more pieces of furniture or mobility devices.

17. A sensor for determining standing usage of a platform, comprising:
    a plurality of sensors integrated with the platform performing measurements configured to detect a user proximate the plurality of sensors of the platform, a position, and an orientation of the user;
    a logic engine in communication with the plurality of sensors that identifies the user and analyzes the measurements and communicate usage information of the platform to one or more designated parties including at least a time period the user is proximate the platform, position, and orientation of the user, the orientation further indicates the posture of the user.

18. A sensor of a standing desk, comprising
    a processor executing a set of instructions; and
    a memory storing the set of instructions, wherein the set of instructions are executed to:
    detect and identify a user proximate the standing desk;
    determine a position and an orientation of the user, the orientation further indicates the posture of the user;
    detect time periods associated with the position and the orientation of the user; and
    report the time periods associated with the position and the orientation of the user.

19. The sensor of claim 18, wherein the user is detected utilizing an electronic device worn by the user that communicates with the sensor of the standing desk.

20. The sensor of claim 18, further comprising:
    sending an alert regarding the status of the user with regard to the standing desk.

* * * * *